US010307225B2

(12) United States Patent
Aravena et al.

(10) Patent No.: US 10,307,225 B2
(45) Date of Patent: Jun. 4, 2019

(54) DENTAL IMPLANT WITH PROGRESSIVE THREAD

(71) Applicant: Implant Direct Sybron International LLC, Thousand Oaks, CA (US)

(72) Inventors: Ines Aravena, Santa Rosa Valley, CA (US); Philippe Khayat, Paris (FR)

(73) Assignee: Implant Direct Sybron International LLC, Thousand Oaks, CA (US)

( * ) Notice: Subject to any disclaimer, the term of this patent is extended or adjusted under 35 U.S.C. 154(b) by 0 days.

(21) Appl. No.: 15/206,357

(22) Filed: Jul. 11, 2016

(65) Prior Publication Data
US 2018/0008382 A1 Jan. 11, 2018

Related U.S. Application Data (60) Provisional application No. 62/191,744, filed on Jul. 13, 2015.

(51) Int. Cl.
*A61C 8/00* (2006.01)
*A61C 13/00* (2006.01)

(52) U.S. Cl.
CPC ........ *A61C 8/0025* (2013.01); *A61C 13/0006* (2013.01); *A61C 13/0022* (2013.01)

(58) Field of Classification Search
CPC .............. A61C 8/0025; A61C 13/0006; A61C 13/0022; A61C 8/00; A61C 8/0022
USPC ................................................ 433/172–174
See application file for complete search history.

(56) References Cited

U.S. PATENT DOCUMENTS

| | | | |
|---|---|---|---|
| 2004/0121289 A1 | 6/2004 | Miller | |
| 2007/0099153 A1* | 5/2007 | Fromovich | A61C 8/0022 433/174 |
| 2010/0009316 A1* | 1/2010 | Hurson | A61C 8/0018 433/173 |
| 2010/0055645 A1* | 3/2010 | Mullaly | A61C 8/0025 433/174 |
| 2010/0304335 A1 | 12/2010 | Garcia Saban et al. | |
| 2012/0232600 A1* | 9/2012 | Wen | A61B 17/863 606/315 |

(Continued)

FOREIGN PATENT DOCUMENTS

WO 2010006740 A2 1/2010

OTHER PUBLICATIONS

European Patent Office, Extended Search Report in Corresponding European Application No. EP16001542.6, dated Nov. 28, 2016, 7 pages.

(Continued)

*Primary Examiner* — Heidi M Eide
(74) *Attorney, Agent, or Firm* — Wood Herron & Evans LLP (57) ABSTRACT

A dental implant includes a screw body and screw threads. The screw body has an apical end and a coronal end. Screw threads include a primary thread and a secondary thread, which overlap in at least a portion of the screw thread. Thread depth progressively increases from the coronal end to the apical end. The coronal end may contain any suitable secondary characteristics, such as machined threads, grooves, micro-threads, or any other characteristics favorable to successful outcomes with dental implant treatment. A method of making such a dental implant is also disclosed.

9 Claims, 6 Drawing Sheets (56) References Cited

U.S. PATENT DOCUMENTS

2012/0237898 A1\* 9/2012 Palti ..................... A61C 8/0025
433/174
2016/0206406 A1\* 7/2016 Andler ................. A61C 8/0022

OTHER PUBLICATIONS

Daraeighadikolaie, A. & Shokri, M., "Measurement of Primary and Secondary Stability of Dental Implants by Resonance Frequency Analysis Method in Mandible." International Journal of Dentistry, vol. 2013, Article ID 506968, 2013, 5 pages.

Ryu, H., Namgung, C., Lee, J. & Lim, Y. "The influence of thread geometry on implant osseointegration under immediate loading: a literature review." Retrieved Jun. 15, 2015, from http://www.ncbi.nlm.nih.gov/pmc/articles/PMC4279055/.

European Patent Office, Office Action in EP Application No. 16001542.6, dated Dec. 17, 2018.

\* cited by examiner

ID=10307225B2">
DENTAL IMPLANT WITH PROGRESSIVE THREAD

TECHNICAL FIELD

The present invention relates generally to dental implants and, more particularly, to dental implants with a progressive V-shaped thread.

BACKGROUND

Edentulism, the condition of being toothless to some extent, may be treated by the implantation of a dental assembly. These assemblies require certain components to rest comfortably and securely in the patient's oral cavity. The implant fixture, also known as the dental implant or simply the implant, is the part of the dental assembly that becomes fused with the patient's jaw bone. The implant is available in both cylinder and screw-type varieties and is typically made from titanium or a titanium alloy. Implant abutments are screwed onto the implant and are positioned at and above the patient's gum line. Finally, a dental prosthesis is placed over the abutment and is designed to look and function like a natural tooth.

Thus, for the dental prosthesis to function as intended, the implant, which is the first component added to the patient's oral cavity, must be positioned with precision and in such a manner that it is securely bonded to the jaw bone until the process of osseointegration is complete. Screw-type implants (also called "implant screws") enjoy widespread clinical use, in part, because they are capable of being securely fastened to the jaw bone. Implant screws are inserted into the jaw bone by linear motion through rotation after a uniform bore hole is pre-drilled into the bone.

Figure 1:
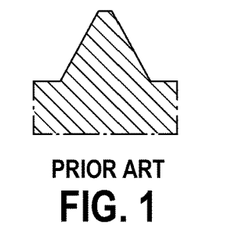
FIG. 1 is a schematic view of a typical V-thread.
Figure 2:
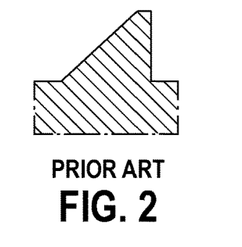
FIG. 2 is a schematic view of a typical buttress thread.
Figure 3:
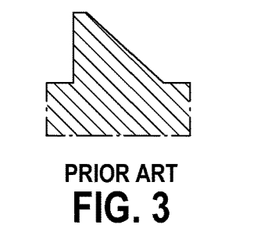
FIG. 3 is a schematic view of a typical reverse buttress thread.
Figure 4:
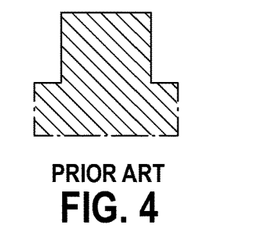
FIG. 4 is a schematic view of a typical square-shaped thread.

Implant screws can be separated into one of four basic categories, as shown in FIGS. 1-4, based on the geometry of their threads: V-shaped, buttress, reverse buttress, and square-shaped. These various geometries are defined by the thread thickness and face angle. V-shaped threads have symmetric sides inclined at equal angles, generally 60°, as shown in FIG. 1. Implant screws with buttress threads have non-symmetrical sides with one face perpendicular to the axis of the screw head, or nearly so, and the other face slanted relative to the same axis at a larger angle, typically 45°. Implant screws with reverse buttress threads merely reverse the arrangement of these faces. See FIGS. 2 and 3. Square-shaped implant screws have threads with symmetrical sides perpendicular to the axis of the screw head, as shown in FIG. 4. Many practitioners prefer V-shaped threads because they provide superior surface area contact between the implant and bone, thus providing greater strength of the bond until osseointegration can take place.

Figure 5:
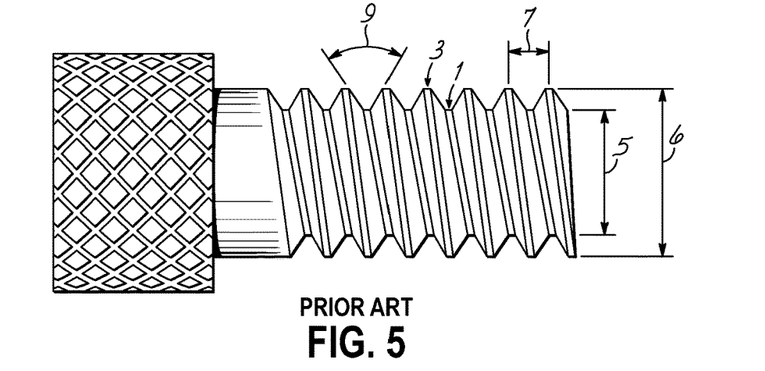
FIG. 5 is a diagrammatic side view of a conventional V-shape threaded dental implant.

FIG. 5 is a diagrammatic depiction of a conventional implant screw having V-shaped threads. The V-shaped threads are composed of root 1 and crest 3. This arrangement results in both a minor diameter 5, measured from root to root perpendicular to the screw's longitudinal axis, and a major diameter 6, measured from crest to crest perpendicular to the same axis. Pitch 7 is the distance between crest 3 and either of the two adjacent crests. The thread angle 9 is defined by the angle of opposing faces of the V-shaped threads when radiating from the root 1 to the crest 3.

Implant screws may have either a straight or tapered body. With straight body implant screws, the central body maintains a consistent, or nearly consistent, diameter throughout the length of the screw, from the screw head (or coronal neck) to the apical end of the screw. With tapered implant screws, the body diameter decreases from the coronal neck to the apical end of the screw to form a conical screw body. The tapered screw body, which is slightly larger in outer diameter than that of the pre-drilled uniform bore hole, grips the bone in a manner that compresses the bone to enhance stability. This tapered design may also be advantageous when the implant screw is placed in close proximity to the root of an adjacent tooth.

Figure 6:
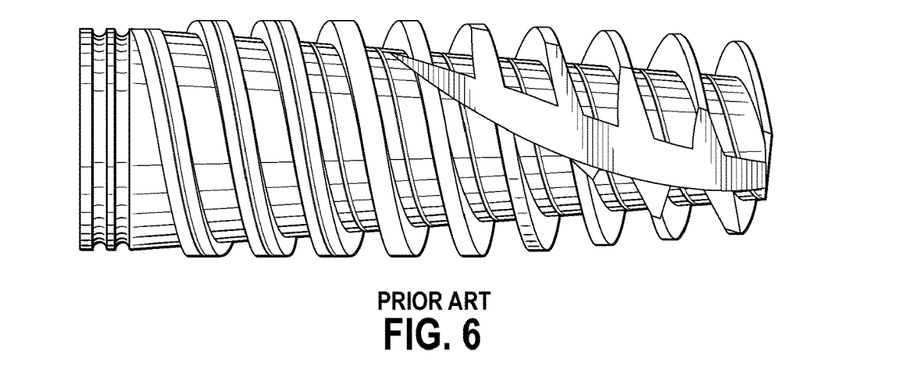
FIG. 6 is a diagrammatic side view of a tapered implant screw with progressive threading.

Thread depth is defined as the distance from the crest 3 of the thread to the root 1 of the thread. See FIG. 5. Many practitioners prefer to use implant screws with variable depths. Variable thread depths are advantageous because shallower thread depths are believed to allow an easier implant procedure, while deeper thread depths are believed to increase the functional surface area at the bone-implant interface, thus strengthening the connection between the implant and bone until osseointegration can occur. Therefore, progressive threads have been developed that increase in depth from the coronal neck of the implant screw to its apical end. Tapered implant screws with progressive threads, as shown in FIG. 6, often have threading with a major diameter 6 that is constant, or nearly constant, from one end of the screw to the other, while the minor diameter 5 decreases from the coronal neck of the implant screw to the apical end. Stated differently, in tapered implant screws with progressive threads, the angle of the taper may coincide with the change in thread depth, although such a correlation is not required. Alternatively, both the major and minor diameters 6, 5 may taper from the coronal neck to the apical end, with the taper of the minor diameter 5 being at a greater angle than that of the major diameter 6.

Figure 7:
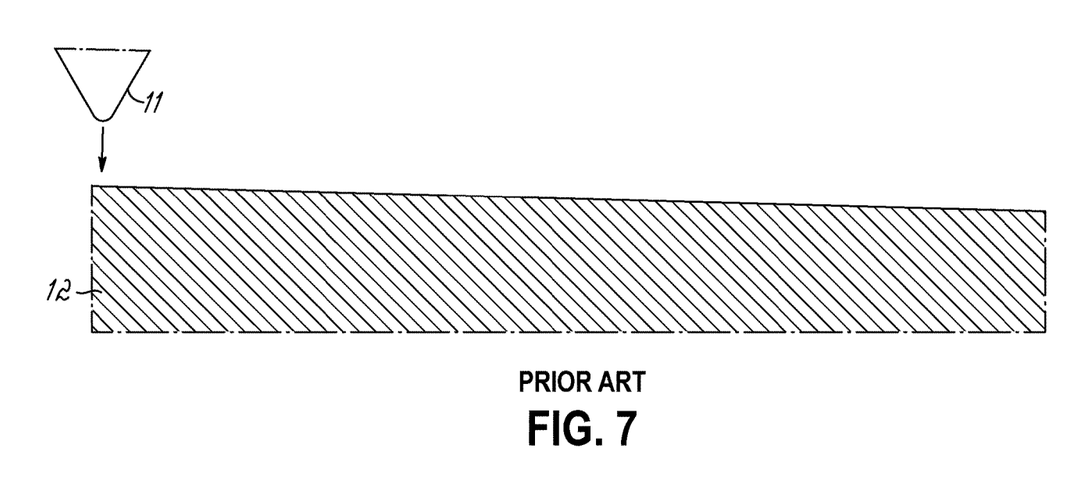
FIG. 7 is a schematic view of a pre-threaded implant screw.
Figure 8:
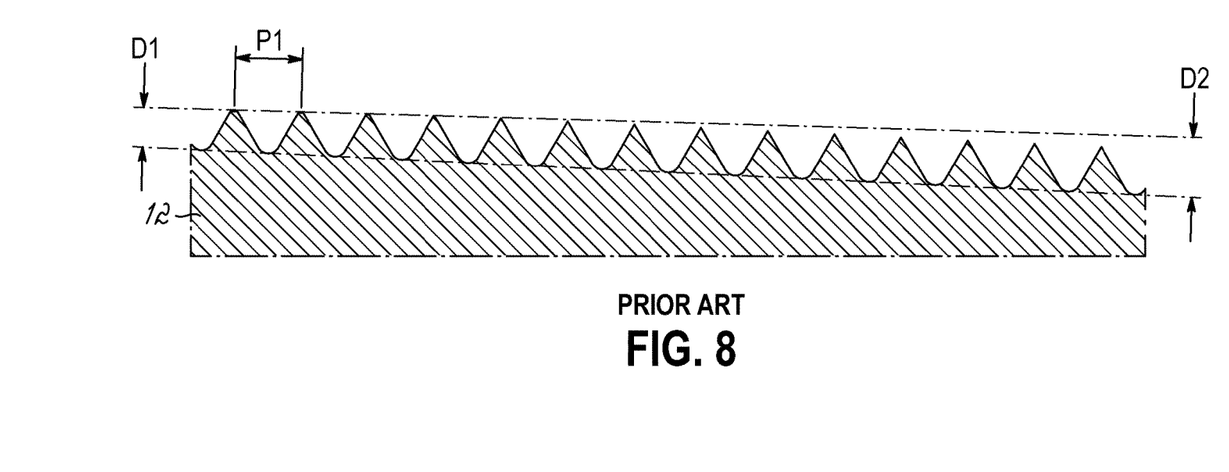
FIG. 8 is a schematic view of a progressively threaded implant screw with V-threads in which the cutting process has destroyed the crest of the threads adjacent to an apical end of the screw.

Progressive threading has been attained with square-shaped, buttress, and reverse-buttress thread types. However, manufacturing issues have, until the present invention, limited the use of progressive threading with V-shaped threads, which are popular among practitioners. In the manufacture of the screw, the process of which is schematically illustrated in FIGS. 7 and 8, as the thread cutting surface 11, which has a triangular cross-sectional geometry complimentary to the desired thread angle, is pushed deeper into the screw body 12, to a depth ranging from D1 to D2, the cutting surface 11 encroaches into the V-thread, as best shown in FIG. 8. Thus, when maintaining a constant thread pitch P1, the distance between two adjacent threads, at sufficiently high depth, the crest of the thread would be cut away, destroying the desired outer diameter of the screw. Therefore, the use of V-shaped threads on a progressive implant platform has generally not been utilized.

Therefore, there is a need for a dental implant with a V-shaped thread type that addresses the present challenges and characteristics discussed above in regard to progressive threads.

SUMMARY OF INVENTION

To these ends, a dental implant is provided with a screw body and at least one screw thread. The screw body has an apical end and a coronal end. The screw thread includes a primary thread configuration and a secondary thread configuration, which overlap in at least a portion of the screw thread. The thread depth progressively increases from the coronal end to the apical end.

In another embodiment a method of making a dental implant is provided. The method includes providing a cylindrical or conical feedstock; applying at least one first cut path to set an upper limit of a depth that increases from the coronal end to the apical end; and applying at least one second cut path along the first cut path to set a lower limit of the depth.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain various aspects of the invention.

DETAILED DESCRIPTION

Although the invention will be described next in connection with certain embodiments, the invention is not limited to practice in any one specific type of dental implant. The description of the embodiments of the invention is intended to cover all alternatives, modifications, and equivalent arrangements as may be included within the spirit and scope of the invention as defined by the appended claims. In particular, those skilled in the art will recognize that the components of the embodiments of the invention described herein could be arranged in multiple different ways.

Figure 9:
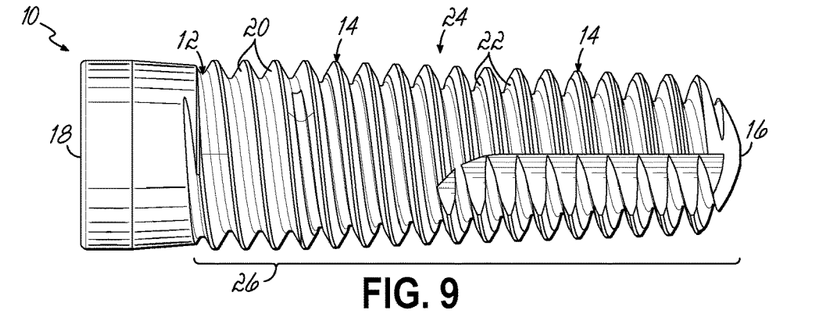
FIG. 9 is a diagrammatic side view of one embodiment of the dental implant with V-threads and progressive threading.

With reference to FIG. 9, a dental implant 10 is shown with screw body 12 and at least one screw thread 14. The screw body 12 has an apical end 16 and a coronal end 18. Screw thread 14 include primary thread configuration 20 and secondary thread configuration 22. Thread depth progressively increases from the coronal end 18 to the apical end 16, as the diameter of the screw body 12 tapers from the coronal end 18 to the apical end 16. Coronal end 18 may contain any suitable secondary characteristics, such as machined threads, grooves, micro-threads, or any other characteristics favorable to successful outcomes with dental implant treatment. No secondary characteristics are shown in FIG. 9, but one of ordinary skill in the art is capable of selecting the appropriate coronal end features for the particular application.

The dental implant may be made from any suitable material. For instance, the dental implant may be made of titanium, the metallic element from group 4 of the periodic table, or a titanium alloy. The human body tolerates sufficiently-pure titanium well, which pure titanium does not cause allergic or foreign body reactions. Indeed, titanium forms a molecular bond with bone in a manner unlike most other materials. Therefore, osseointegration of these implants may be viewed as the formation of molecular bonds between the jaw bone of the patient and the titanium implant. Thus, with greater osseointegration, the connection between the bone and the implant is stronger.

Dental implant 10 may be of any desired length from coronal end 18 to apical end 16. For instance, the length of the dental implant 10 may range from about 3 mm to about 18 mm. This length may be about 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, or any fractional portion thereof. In certain embodiments, the length of the dental implant 10 may be about 6 mm, 8 mm, 10 mm, 11.5 mm, 13 mm, or 16 mm.

Dental implant 10 may be of any desired diameter. For instance, this diameter may range from about 3 mm to about 7 mm. This diameter may be about 3 mm, 4 mm, 5 mm, 6 mm, 7 mm, or any fractional portion thereof.

The included angle $a_1$ of the primary thread configuration 20 may be any suitable thread angle. For instance, the included angle $a_1$ of the primary thread configuration 20 may range between about 45° and about 75°, between about 50° and about 70°, or between about 55° and about 65°. In one embodiment, the included angle of the primary thread configuration 20 may be about 60°. The included angle $a_2$ of the secondary thread configuration 22 is generally less than the included angle of the primary thread configuration 20. For instance, the included angle $a_2$ of the secondary thread configuration 22 may range from between about 15° and about 60°, between about 20° and about 50°, or between about 25° and 35°. In one embodiment, the included angle of the secondary thread configuration may be about 30°.

The thread pitch of the dental implant of the present invention is not particularly limited. For instance, the thread pitch may range from about 0.2 mm to about 2 mm, from about 0.5 mm to about 1.5 mm, or from about 0.6 mm to about 1 mm. In certain embodiments, the thread pitch may be about 0.6 mm, 0.7 mm, 0.8 mm, 0.9 mm, or 1.0 mm. A common thread pitch used in the industry is 0.6 mm. The thread pitch may be relatively uniform throughout the threaded portion of the dental screw or may be variable.

Figure 10:
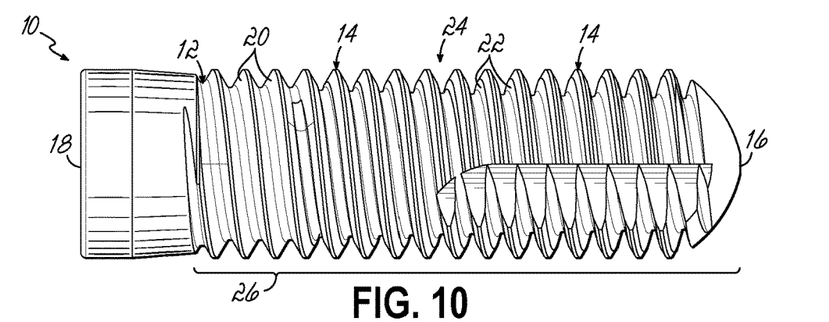
FIG. 10 is a diagrammatic side view of a second embodiment of the dental implant with V-threads and progressive threading.

The arrangement of the primary thread configuration 20 and secondary thread configuration 22 on screw body 12 is not particularly limited. FIGS. 9-12 provide exemplary embodiments of the dental implant 10. In FIGS. 9 and 10, the primary thread configuration 20 is present near the coronal end 18 of the dental implant 10. Then, a portion of the primary thread configuration 20 is present in the midsection 24 and near the apical end 16 along with the progressively deeper secondary thread configuration 22, which is also present in the midsection 24 and near the apical end 16 of the dental implant 10. A difference between FIGS. 9 and 10 is that the screw body 12 is tapered in FIG. 9 and straight in FIG. 10, although both show a progressive thread.

Figure 11:
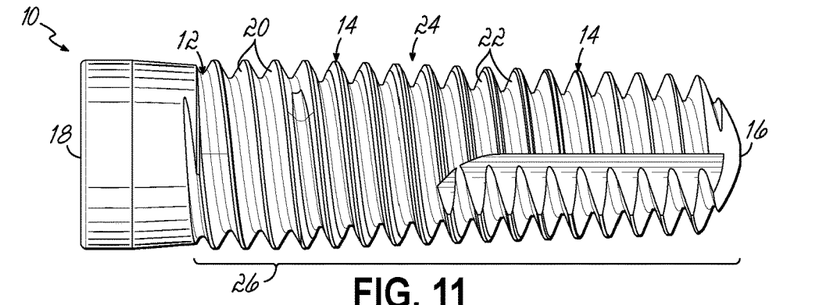
FIG. 11 is a diagrammatic side view of a third embodiment of the dental implant with V-threads and progressive threading.

Turning now to FIG. 11, just as in FIGS. 9 and 10, the primary thread configuration 20 is present near the coronal end 18 and the progressively deeper secondary thread configuration 22 is present in the midsection 24 with the primary thread configuration 20, but in this embodiment, only secondary thread 22 is present near the apical end 16, not the primary thread configuration 20.

Figure 12:
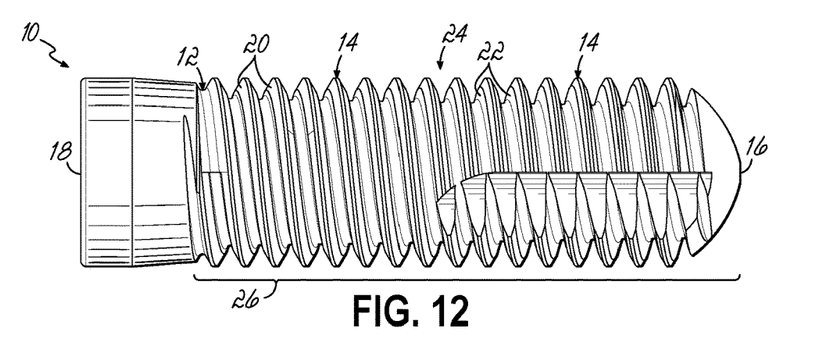
FIG. 12 is a diagrammatic side view of a fourth embodiment of the dental implant with V-threads and progressive threading.

Alternatively, as shown in FIG. 12, the primary thread configuration 20 may be coupled with the secondary thread configuration 22 throughout the threaded body 26. The coronal end 18 and apical end 16 both include the primary thread configuration 20 and the secondary thread configuration 22.

The dental implant of the invention may have single lead threads or multiple lead threads. In the embodiments shown in FIGS. 9-12, the threads are double lead threads, meaning there are two starts for the primary thread configuration 20. Similarly, the secondary thread configuration 22 may be single lead or multiple lead.

Figure 13:
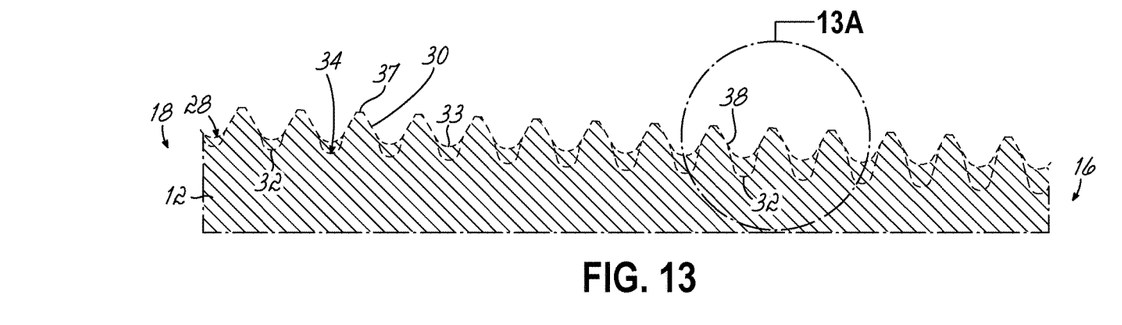
FIG. 13 is a schematic diagram of a method of making a dental implant with V-threads and progressive threading.
Figure 13A:
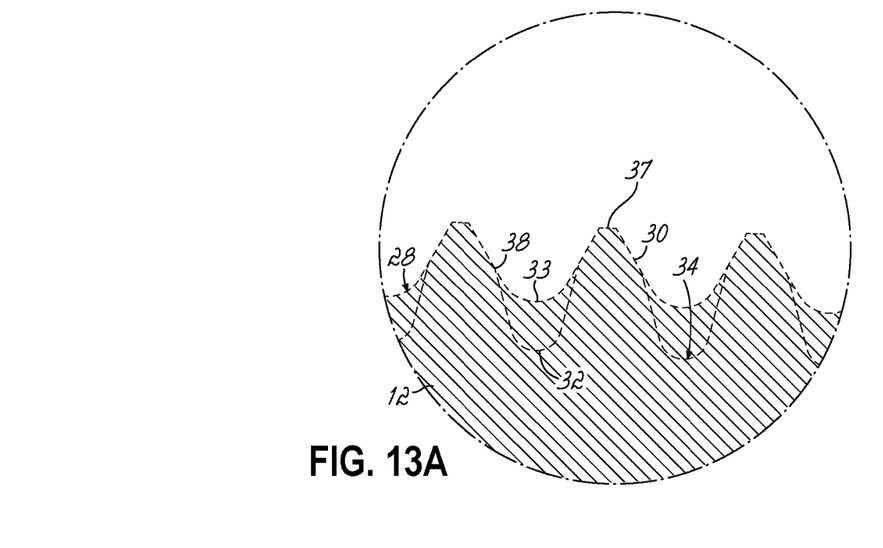
FIG. 13A is an enlarged view of the circled region of FIG. 13.
Figure 14:
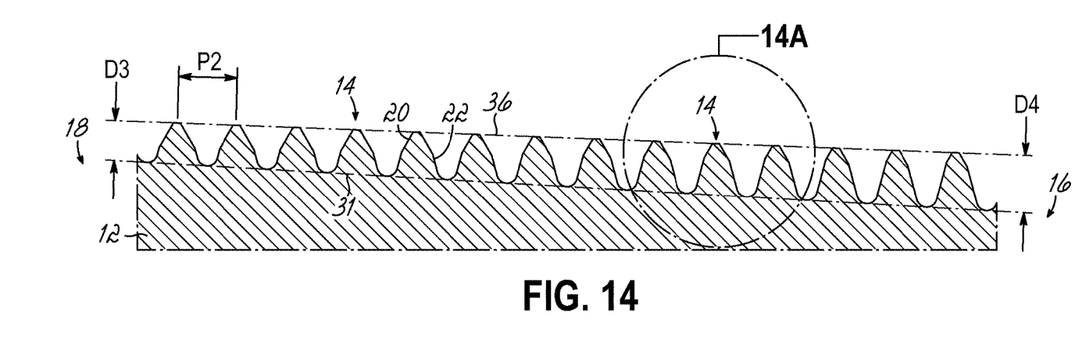
FIG. 14 is a schematic view of a progressively threaded implant screw with V-threads in accordance with the invention.
Figure 14A:
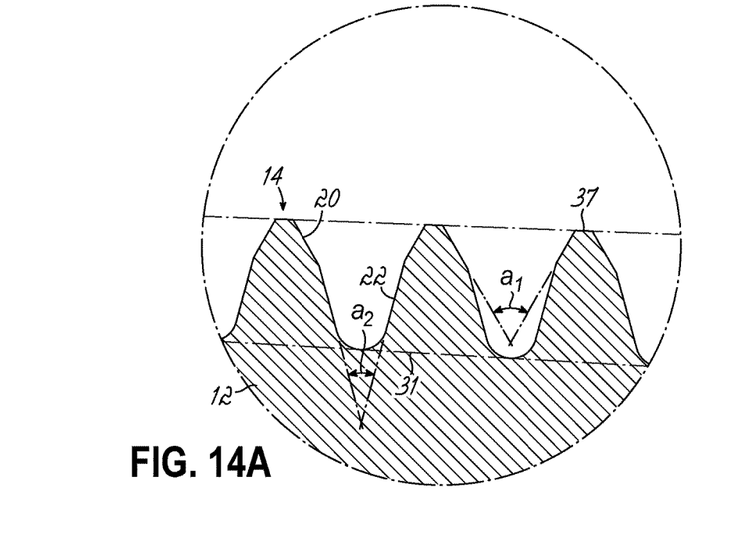
FIG. 14A is an enlarge view of the circled region of FIG. 14.

The dental implants of the present invention may be manufactured analogously to the process described above as to FIGS. 7 and 8. In FIGS. 13-14A, first cut path 28 creates intermediate threads 30, the upper limit 36 which is determined by the major diameter of the stock material, and the lower limit 33 establishes an intermediate root. The upper limit defines the crest 37 of the final thread. Second cut path 34 completes the formation of screw thread 14, setting the pitch P2 and the lower limit 31 of the depth ranging from D3 to D4. The distance between lower limit 33 of first cut path 28 and lower limit 32 of second cut path 34 increases from the coronal end 18 to the apical end 16. As best shown in FIG. 14, the two cut paths 28, 34 create primary thread configuration 20 and secondary thread configuration 22. FIGS. 13A and 14A provide an enlarged view of a portion of the thread. During manufacture of the embodiment shown in FIGS. 13-14A, intersection point 38 between cut paths 28 and 34 also represents the interface between primary thread configuration 20 and secondary thread configuration 22, and the lower limit 31 of the depth is formed solely from second cut path 34.

Figure 15:
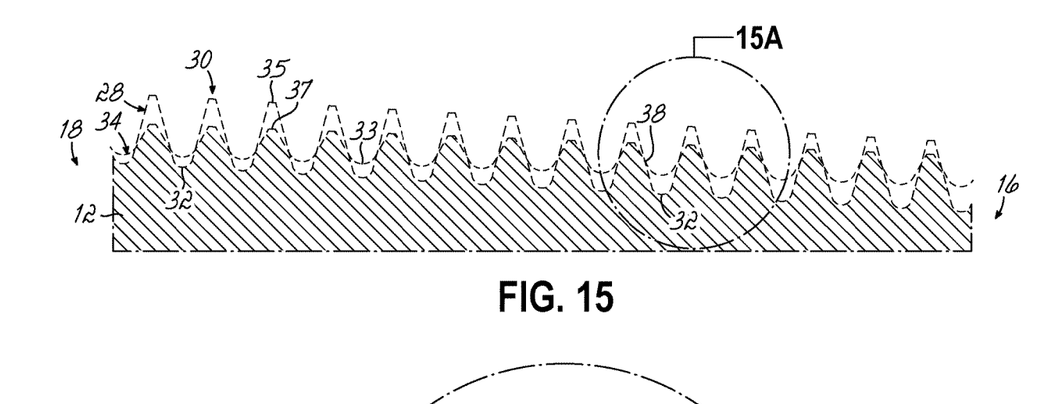
FIG. 15 is a schematic diagram of an alternative method of making a dental implant with V-threads and progressive threading.
Figure 15A:
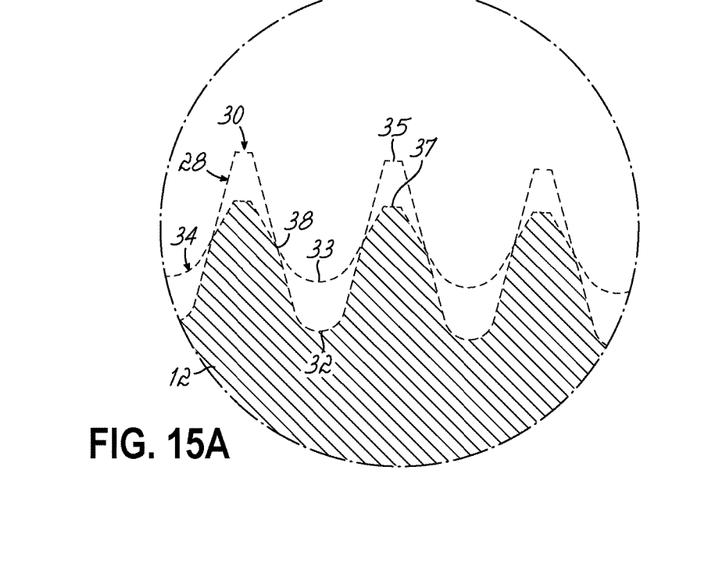
FIG. 15A is an enlarged view of the circled region of FIG. 15.

Cut paths 28 and 34 may be applied in either order. Thus, as shown in FIGS. 15 and 15A, where like labels refer to like features, first cut path 28 creates intermediate thread 30, the upper limit of which is determined by the major diameter of the stock material and establishes an intermediate crest 35, and the lower limit 31. The second cut path 34 completes the formation of the screw thread 14, setting the upper limit 36. Furthermore, in the case of multiple lead threads, multiple first cut paths 28 and second cut paths 34 may be applied.

The implants are placed using conventional methods. First, the dental practitioner accesses the jawbone of an anesthetized patient by using either a scalpel to create flaps from the gum tissue or a circular tissue punch with a diameter slightly larger than that of the planned implant. Next, a pilot hole is created in the bone tissue using a series of drills of increasing diameter. The dental practitioner may then create threads in the newly formed bore hole matching those of the planned implant using a screw tap, if applicable. The implant is placed into the void using a dental driver with an appropriate adapter or a hand wrench, such as a torque wrench. Finally the surgical site is closed or a healing/temporary abutment is assembled onto the implant to remain during the osseointegration process.

The deeper progressive threads of the invention allow for the use of undersized step-down drills. Thus, the implant experiences better apical bone engagement while preventing excessive bone condensation near the apical tip of the implant.

While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be from such details without departing from the scope of the general inventive concept.

What is claimed is:

1. A dental implant having an apical end and a coronal end, the dental implant comprising:
   a screw body; and
   at least one screw thread defining a root and a crest,
   wherein the at least one screw thread comprises a coronal portion situated near the coronal end, an apical portion situated near the apical end, and an intermediate portion situated between the coronal portion and the apical portion,
   wherein along the coronal portion, the at least one screw thread consists of a primary thread configuration from the root to the crest,
   wherein along the intermediate portion, the at least one screw thread comprises a secondary thread configuration from the root to an intermediate position between the root and crest, and the primary thread configuration from the intermediate position to the crest,
   wherein along the apical portion, the at least one screw thread comprises either: a) the secondary thread configuration from the root to the intermediate position between the root and the crest, and the primary thread configuration from the intermediate position to the crest; or b) the secondary thread configuration from the root to the crest,
   wherein the at least one screw thread becomes progressively deeper from the coronal end to the apical end, and
   wherein the primary thread configuration defines a first included angle and the secondary thread configuration defines a second included angle different from the first included angle.

2. The dental implant of claim 1, wherein the at least one screw thread is a multi-lead thread.

3. The dental implant of claim 1, wherein the at least one screw thread is a single lead thread.

4. The dental implant of claim 1, wherein the at least one screw thread has a thread pitch of about 0.6 mm.

5. The dental implant of claim 1, wherein the first included angle is about 60°.

6. The dental implant of claim 1, wherein the second included angle is about 30°.

7. The dental implant of claim 1, wherein the at least one screw thread is V-shaped.

8. A dental implant having an apical end and a coronal end, the dental implant comprising:
a screw body; and
at least one screw thread defining a root and a crest and becoming progressively deeper from the coronal end to the apical end,
wherein the at least one screw thread comprises a coronal portion situated near the coronal end, an apical portion situated near the apical end, and an intermediate portion situated between the coronal portion and the apical portion,
wherein along the coronal portion, the at least one screw thread comprises a primary thread configuration from the root to the crest,
wherein along the intermediate portion and the apical portion, the at least one screw thread comprises a secondary thread configuration from the root to an intermediate position between the root and the crest and the primary thread configuration from the intermediate position to the crest, and
wherein the primary thread configuration defines a first included angle and the secondary thread configuration defines a second included angle different from the first included angle, and wherein along the coronal portion, the first included angled extends from the root to the crest.

9. A dental implant having an apical end and a coronal end, the dental implant comprising:
a screw body; and
at least one screw thread defining a root and a crest and becoming progressively deeper from the coronal end to the apical end,
wherein the at least one screw thread comprises a coronal portion situated near the coronal end, an apical portion situated near the apical end, and an intermediate portion situated between the coronal portion and the apical portion,
wherein along the coronal portion, the at least one screw thread comprises a primary thread configuration from the root to the crest,
wherein along the intermediate portion, the at least one screw thread comprises a secondary thread configuration from the root to an intermediate position between the root and the crest and the primary thread configuration from the intermediate position to the crest,
wherein along the apical portion, the at least one screw thread comprises the secondary thread configuration from the root to the crest, and
wherein the primary thread configuration defines a first included angle and the secondary thread configuration defines a second included angle different from the first included angle, and wherein along the coronal portion, the first included angled extends from the root to the crest.

* * * * *